US008828972B2

(12) United States Patent
Eibl et al.

(10) Patent No.: US 8,828,972 B2
(45) Date of Patent: Sep. 9, 2014

(54) FORMULATIONS CONTAINING ALKYLPHOSPHOCHOLINES USING NOVEL NEGATIVE CHARGE CARRIERS

(75) Inventors: Hansjörg Eibl, Bovenden (DE); Susanne Christine Wieland-Berghausen, Weil am Rhein (DE); Jean Steffan, Mulhouse (FR)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 961 days.

(21) Appl. No.: 11/577,518

(22) PCT Filed: Oct. 19, 2005

(86) PCT No.: PCT/EP2005/011252
§ 371 (c)(1),
(2), (4) Date: Jul. 20, 2007

(87) PCT Pub. No.: WO2006/042751
PCT Pub. Date: Apr. 27, 2006

(65) Prior Publication Data
US 2008/0090781 A1 Apr. 17, 2008

(30) Foreign Application Priority Data

Oct. 19, 2004 (DE) .......................... 10 2004 050 910
Nov. 16, 2004 (DE) .......................... 10 2004 055 284

(51) Int. Cl.
*A61K 47/28* (2006.01)
*A61K 31/201* (2006.01)
*A61K 31/685* (2006.01)
*A61K 9/127* (2006.01)
*C07F 9/09* (2006.01)
*C07F 9/10* (2006.01)
*A61K 47/12* (2006.01)
*A61K 47/18* (2006.01)
*A61K 47/24* (2006.01)

(52) U.S. Cl.
CPC ............ *A61K 9/1272* (2013.01); *A61K 31/201* (2013.01); *A61K 31/685* (2013.01); *A61K 47/12* (2013.01); *A61K 47/18* (2013.01); *A61K 47/24* (2013.01); *A61K 47/28* (2013.01); *C07F 9/091* (2013.01); *C07F 9/10* (2013.01)
USPC .............................. 514/77; 514/560; 514/766

(58) Field of Classification Search
CPC .... A61K 47/28; A61K 31/201; A61K 31/685
See application file for complete search history.

(56) References Cited

U.S. PATENT DOCUMENTS 4,356,167 A * 10/1982 Kelly .............................. 424/450
4,615,885 A * 10/1986 Nakagame et al. ........ 424/94.63
5,049,391 A * 9/1991 Suzuki et al. ................. 424/450
5,711,964 A * 1/1998 Dattagupta et al. ........... 424/450
2003/0199476 A1 * 10/2003 Eibl ................................ 514/78

FOREIGN PATENT DOCUMENTS

| DE | 41 32 345 A1 | 4/1993 |
| EP | 0 615 746 A1 | 9/1994 |
| JP | 1-180245 A | 7/1989 |
| JP | 2000-247868 A | 9/2000 |
| WO | 9426730 A2 | 11/1994 |
| WO | WO 96/11670 A | 4/1996 |
| WO | 9816200 A1 | 4/1998 |
| WO | 0033917 A1 | 6/2000 |
| WO | WO 01/11069 * | 2/2001 |
| WO | WO 01/72289 A2 | 10/2001 |
| WO | WO 03/028736 A2 | 4/2003 |

OTHER PUBLICATIONS

English translation of WO 03/028,736 (Machine translated at http://ep.espacenet.com/?locale=EN_ep on Apr. 1, 2010).*
Kaufmann-Kolle et al. Drugs of Today, 1998, vol. 34, Suppl. F, pp. 107-115.*
Duzgunes et al., "Proton-Induced Fusion of Oleic-Acid-Phosphatidylethanolamine Liposomes", Biochemistry, vol. 24, No. 13, 1985, pp. 3091-3098.
Connor et al., "PH Sensitive Liposomes Acid Induced Liposome Fusion", Proceedings of the Natural Academy of Sciences of the US, vol. 81, No. 6, 1984, pp. 1715-1718.
Eue, I., "Growth Inhibition of Human Mammary Carcinoma by Liposomal Hexadecylphosphocholine; Particpation of Activated Macrophages in the Antitumor Mechanism", Int. Journal of Cancer, 2001, vol. 92, No. 3, pp. 426-433.
Luckenbach G., "Liposomally Activated Macrophages: Subsequent Interaction with L12010 Leukemic Cells", Albrecht et al., Intern Journal of Cancer, 1981, vol. 27, No. 6, 837-839.
Perkins W.R. et al., "Combination of Antitumor Ether Lipid with Lipids of Complementary Molecular Shape Reduces its Hemolytic Activity", Biochimica et Biophysica Acta, 1997, vol. 1327, No. 1, pp. 61-68.
Seifert K. et al., "Effects of Miltefosine and Other Alkylphosphocholines on Human Intestinal Parasite *Entamoeba histolytica*", Antimicrobial Agents and Chemotherapy, 2001, vol. 45, No. 5, pp. 1505-1510.

* cited by examiner

Primary Examiner — James D Anderson
(74) Attorney, Agent, or Firm — Rothwell, Figg, Ernst & Manbeck, P.C.

(57) ABSTRACT

The invention relates to novel medicament formulations containing, as active ingredients, alkylphosphocholines and the like, alkyl-alkanediol-phosphocholines and the like, and (ether)lysolecithins and the like, in different forms of embodiment. The active ingredients are integral constituents of liposomes, also containing cholesterol and the like and a negative charge carrier. The medicament formulations are especially suitable for the treatment and/or prophylaxis of cancer, protozoan diseases such as leishmaniasis and amoebic diseases, acariasis and diseases caused by arthropods, and bacterial diseases, such as ehrlichiosis. Ocular diseases accompanied by uncontrolled cellular processes can also be advantageously influenced.

8 Claims, No Drawings

FORMULATIONS CONTAINING ALKYLPHOSPHOCHOLINES USING NOVEL NEGATIVE CHARGE CARRIERS

CROSS REFERENCE TO RELATED APPLICATION

This application is a 35 USC §371 National Phase Entry Application from PCT/EP2005/011252, filed Oct. 19, 2005, and designating the United States.

The present invention relates to novel pharmaceutical formulations containing alkylphosphocholine compounds both as active ingredients and as integral constituents of liposomes. The pharmaceutical formulations are particularly suitable for the treatment and/or prophylaxis of tumour diseases, of diseases caused by rapidly proliferating cells and of protozoan diseases, in particular of leishmaniasis and amoebic diseases, of acarinosis and diseases caused by arthropods. However, these formulations can also be used successfully for the treatment of bacterial diseases such as, for example, ehrlichiosis. Ocular diseases associated with uncontrolled cellular processes can also be successfully treated using these formulations.

Alkylphosphocholine compounds have an antiproliferative effect and are highly effective against tumour and protozoan diseases. However, a major drawback of these compounds is, firstly, that especially those compounds containing relatively long-chain hydrocarbon radicals have poor solubility in aqueous solutions, rendering them unsuitable both for intravenous (IV) administration and for oral administration in the form of drinking solutions. Furthermore, the compounds are often only poorly resorbed or not resorbed at all when administered orally. Many of these effective compounds also have considerable side effects preventing them from being administered in high doses over a relatively long period of time. The toxicity side effects are based to a large extent on the haemolytic effect of the compounds.

Protozoa are single-cell creatures, some of which are pathogenic parasites. The most common representatives affecting humans include plasmodia (malaria), trypanosomes (sleeping sickness), amoebae, for example entamoebae and acanthamoebae (amoebiasis, encephalitis) and *leishmania* (leishmaniasis).

The term "leishmaniasis" refers to various tropical diseases which are caused by protozoa of the *Leishmania* genus and are transmitted by blood-sucking insects. Three types of *leishmania* are currently known, causing very different disease patterns: "kala-azar" affecting the spleen and liver "Aleppo boil" with inflammatory reactions on the skin and "espundia" appearing also on the mucous membranes of the upper respiratory and digestive track. The cause of all three diseases is less characteristic than in other protozoan diseases and in many cases insidious. The incubation period can last for weeks or even months. In untreated cases, very high mortality rates are often observed.

The treatment of leishmaniasis is based substantially still on long-known antimony preparations, mainly sodium stibogluconate (Pentostam). The treatment is usually carried out over two to three weeks but then has to be interrupted for one to two weeks, because common side effects could otherwise reach a threatening degree and become irreversible. The side effects include gastrointestinal irritations, circulatory disturbance ranging to shock and damage to the liver parenchyma. A further drawback found is that there are already strains of *leishmania* that are resistant to antimony. Further pharmacons used include aromatic diamidines, pentamidine and Amphotericin B. However, these compositions are usually used only in combination with antimony compounds and also have considerable side effects.

The following are particularly important amoebae that can affect humans: *Entamoeba histolytica* causes dysentery and hepatic abscesses in humans. The pathogenic agent is very common in many countries, causing approximately 36 to 50 million cases of disease each year and between 40,000 and 110,000 deaths. The life cycle is simple, infection takes place via cysts ingested with contaminated water or contaminated foods. The cysts pass through the stomach unchanged and live in the colon, four trophozoits, the amoebae themselves, being produced from each cyst. In the rectum, some of the trophozoits become cysts again and thus form the spores which can survive outside the human body. In the colon, the trophozoits can live without causing much harm, though they can also attack the intestinal wall. This can result in small lesions of the mucous membrane but also in hemorrhaging ulcers leading to bloody diarrhea, the full-blown case of amoebic dysentery. A further common manifestation of amoebiasis is amoebic hepatic abscesses. In this case, the amoebae advance from the intestine, through the mesenterial vessels into the liver, where they produce large abscesses. Both amoebic hepatic abscesses and intestinal amoebiasis can be fatal if left untreated.

*E. histolytica* trophozoits cannot survive without the human host. In contrast thereto there are free-living amoebae that in rare cases can cause relatively serious diseases in humans. Acanthamoebae (for example *Acanthamoeba castellanii, Acanthamoeba culbertsoni*) can cause chronic granulomatous encephalitis in immunosuppressed patients, and cases of acanthamoebic keratitis are relatively common in people who wear contact lenses. *Naegleria fowleri* is a free-living amoeba flagellate which typically lives in fresh water and can infect bathers. The parasite advances via the nose and the olfactory nerves into the brain and causes peracute meningoencephalitis. Causes of encephalitis caused by acanthamoebae or naegleria are extremely rare but have previously had an extremely poor prognosis.

Chemotherapeutic agents currently used in *E. histolytica* infections include nitroimidazoles, mainly metronidazole.

*E. histolytica* does not have oxidative phosphorylation but rather obtains its energy by glycolysis. The oxidation of the pyruvate to form acetyl-CoA produces in the amoeba reduced ferredoxine which is capable of reducing the nitroimidazole to a nitrosoimidazole. This aggressive substance damages the biomolecules of the amoebae. Humans do not have such an intensively reducing agent and do not transform metronidazole into the more toxic nitrosoimidazole form. To date, there have been no confirmed reports of the proliferation of metronidazole-resistant *E. histolytica* strains. Frequently reported, however, are cases in which metonidazole treatment is said to have been unsuccessful, and partially resistant strains have been generated under laboratory conditions. In the event of a resistance possibly forming, it would be very important to have new substance classes effective against *E. histolytica*, as there is currently no satisfactory alternative to the nitrimidazoles.

In contrast to *E. histolytica*, acanthamoebae and naegleria have mitochondria and can live aerobically. They do not reduce nitroimidazoles and these compounds are therefore completely ineffective. Acanthamoebae are said to be sensitive to rifampicin and paromomycin, naegleria to Amphotericin B, although encephalitides have been cured using free-living amoebae only in a few isolated cases.

DE application P 41 32 344.0-41 discloses processes for the preparation of a pharmaceutical composition which is suitable for oral or topical administration in the treatment of protozoan diseases, in particular leishmaniasis, and contains as an active ingredient one or more compounds of the general formula:

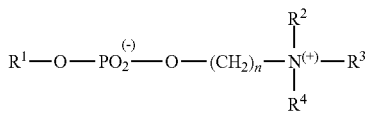

wherein $R^1$ is a saturated or unsaturated hydrocarbon radical containing 12 to 20 carbon atoms, $R^2$, $R^3$ and $R^4$, independently of one another, are H, a $C_1$-$C_5$ alkyl group, a $C_3$-$C_6$ cycloalkyl group or a $C_1$-$C_5$ hydroxyalkyl group, wherein two of $R^2$, $R^3$ and $R^4$ can together form a $C_2$-$C_5$ alkylene group which can optionally be substituted with a —O—, —S— or $NR^5$ group, wherein $R^5$ is H, a $C_1$-$C_5$ alkyl group, a $C_3$-$C_6$ cycloalkyl group or $C_1$-$C_5$ hydroxyalkyl group.

Compounds of this general formula displayed a much higher activity than sodium stibogluconate, especially when applied orally or topically. Nevertheless, relatively high doses frequently led to side effects, such as for example irritation of the gastrointestinal tract, which in test animals led to a loss of appetite and a considerable loss of weight—the body weight of rats was seen to be reduced by more than 25%.

A further drawback of the above-mentioned compounds is that the intravenous administration of alkylphosphocholines having chain lengths of greater than 21 carbon atoms was previously not possible on account of their low water solubility and the intravenous administration of alkylphosphocholines having chain lengths of 21 or fewer carbon atoms was not possible on account of haemolytic effects. In the past, alkylphosphocholine-containing compositions were packed into liposomes for intravenous administration. The liposomes consisted of hexadecylphosphocholine, cholesterol and phosphotidylglycerol or of hexadecylphosphocholine, cholesterol and phosphatidylpolyethylene glycols. However, the preparation of these liposomes is very complex and expensive, as it requires high-pressure moulding or similar processes, and the finished product also has the drawback of being very difficult to filter under sterile conditions.

a) PCT/EP01/03609 describes a pharmaceutical formulation which is a mixture of a phospholipid compound of formula I:

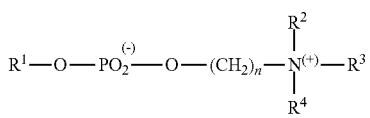

wherein $R^1$ is a saturated or unsaturated hydrocarbon radical containing 16 to 24 carbon atoms, $R^2$, $R^3$ and $R^4$, independently of one another, are H, a $C_1$-$C_5$ alkyl group, a $C_3$-$C_6$ cycloalkyl group or a $C_1$-$C_5$ hydroxyalkyl group, wherein two of $R^2$, $R^3$ and $R^4$ can together form a $C_2$-$C_5$ alkylene group which can optionally be substituted with a —O—, —S— or $NR^5$ group, wherein $R^5$ is H, a $C_1$-$C_5$ alkyl group, a $C_3$-$C_6$ cycloalkyl group or $C_1$-$C_5$ hydroxyalkyl group, n is an integer from 2 to 6, as 30 to 60 mol % active ingredient,
b) 25 to 65 mol % cholesterol and/or a cholesterol derivative and
c) 5 to 15 mol % of a phosphotidylmonoglycerol or phosphotidyloligoglycerol containing at least one oleyl group, a), b) and c) together forming 100 mol % and d) a water-miscible, physiologically acceptable alcohol which contains from 2 to 4 carbon atoms and optionally water, and also optionally conventional pharmaceutical auxiliaries and/or active ingredients, the components being in the form of a complex dispersed in water.

This formulation overcomes some of the above-mentioned drawbacks.

PCT/EP02/10882 describes a pharmaceutical preparation containing a) as an active ingredient from 30 to 60 mol % of a phospholipid compound of formula I:

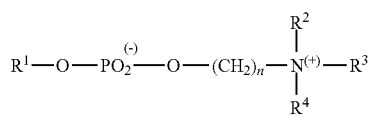

wherein $R^1$ is a saturated or unsaturated, in particular a singly or multiply unsubstituted hydrocarbon radical containing 15 to 24 carbon atoms, in particular containing 16 to 24 carbon atoms, which can optionally contain one or more heteroatoms selected from O, N or S, $R^2$, $R^3$ and $R^4$, independently of one another, are H, a $C_1$-$C_5$ alkyl group, a $C_3$-$C_6$ cycloalkyl group or a $C_1$-$C_5$ hydroxyalkyl group, wherein two of $R^2$, $R^3$ and $R^4$ can together form a $C_2$-$C_5$ alkylene group which can optionally be substituted with a —O—, —S— or $NR^5$ group, wherein $R^5$ is H, a $C_1$-$C_5$ alkyl group, a $C_3$-$C_6$ cycloalkyl group or $C_1$-$C_5$ hydroxyalkyl group, n is an integer from 2 to 6,
b) 10 to 65 mol %, in particular 25 to 65 mol %, cholesterol and
c) 3 to 30 mol %, in particular 5 to 15 mol %, cholesteryl phosphomonoglycerol, cholesteryl phosphooligoglycerol, alkyl phosphoglycerol, alkyl phosphooligoglycerol, alkyl phosphoglycol, alkyl phosphopropanediol-(1,3) and/or alkyl phosphopropanediol-(1,2).

Nevertheless, in particular on account of the commonness and the associated importance of the above-mentioned diseases, there is still a major need for pharmaceutical preparations which can be used successfully for the treatment and/or prophylaxis of these diseases.

There is also a major need for formulations which are suitable for use in animals, in particular in dogs. Formulations developed for use in humans can often not be used in animals, in particular in dogs, as animals react much more sensitively and undesirable side effects often make treatment difficult or impossible.

However, the costs of preparing and developing the pharmaceutical preparation are also important, in particular for the field of veterinary medicine.

An object of the present invention was therefore to provide novel pharmaceutical preparations which can be used successfully for the treatment and/or prophylaxis of the above-mentioned diseases and are suitable, in particular, not only for the treatment of humans but also for the treatment of animals, in particular of dogs.

According to the invention, this object is achieved by a pharmaceutical preparation containing as an active ingredient a) a phospholipid compound of general formula I:

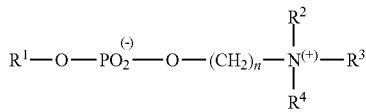

I wherein $R^1$ is a saturated or unsaturated hydrocarbon radical containing 15 to 26 carbon atoms, wherein $R^2$, $R^3$ and $R^4$ are, each time they occur and independently of one another, H, a $C_1$ to $C_6$ alkyl group, a $C_3$ to $C_6$ cycloalkyl group or a $C_2$ to $C_6$ hydroxyalkyl group, wherein two of $R^2$, $R^3$ and $R^4$ can together form a $C_2$ to $C_5$ alkylene group, wherein n is an integer from 2 to 6, or by a pharmaceutical preparation containing as an active ingredient a phospholipid compound of general formula II (alkylphosphocholines containing ring nitrogen):

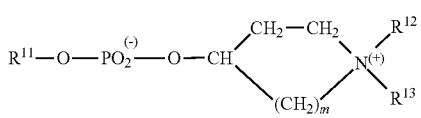

II wherein $R^{11}$ is a saturated, unsaturated or else multiply unsaturated hydrocarbon radical containing 15 to 26 carbon atoms, wherein $R^{12}$ and $R^{13}$ are, each time they occur and independently of one another, H, a $C_1$ to $C_6$ alkyl group or a $C_2$ to $C_6$ hydroxyalkyl group, wherein m is an integer of 1 or 2, or by a pharmaceutical preparation containing as an active ingredient a phospholipid compound of general formula III (alkyl-ethylene glycol-phosphocholines)

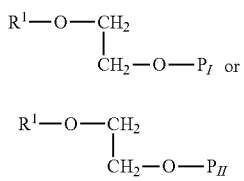

III a

III b wherein $P_I$ is

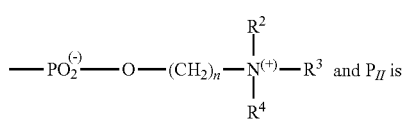

$P_I$ and $P_{II}$ is $P_{II}$ or by a pharmaceutical preparation containing as an active ingredient a phospholipid compound of general formula IV (alkyl-alkanediol-phosphocholines)

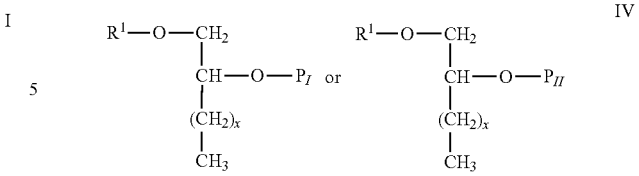

IV wherein the radicals $R^1$ and $P_I$ or $P_{II}$ can also be exchanged for one another, wherein $R^1$, $P_I$ and $P_{II}$ correspond to the above meanings, wherein x is an integer from 0 to 4, or by a pharmaceutical preparation containing as an active ingredient a phospholipid compound of general formula V (ether-lysolecithins)

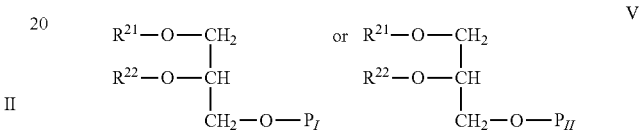

V wherein $R^{21}$ is a saturated or singly or multiply unsaturated hydrocarbon radical containing 15 to 26 carbon atoms, wherein $R^{22}$ denotes a $C_1$ to $C_6$ alkyl group, wherein $P_I$ and $P_{II}$ correspond to the above meanings, wherein the radicals $R^{21}$, $R^{22}$ and $P_I$ or $P_{II}$ can be distributed in any desired manner over the positions in the glycerol molecule, or by a pharmaceutical preparation containing as an active ingredient a phospholipid compound of general formula VI (alkyl-substituted alkanediol-phosphocholines):

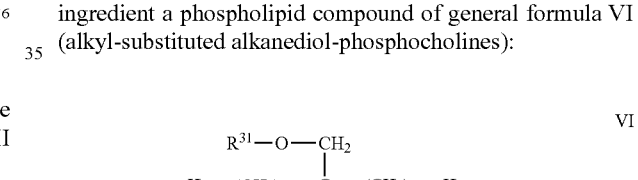

VI wherein $R^{31}$ is a saturated or singly or multiply unsaturated hydrocarbon radical containing 15 to 26 carbon atoms, wherein y and z, independently of one another, can be an integer from 0 to 3, but y and z cannot be 0 simultaneously, wherein $P_I$ and $P_{II}$ correspond to the above meanings, or by a pharmaceutical formulation containing as an active ingredient a phospholipid compound of general formula VII (1-O-alkyl-2-methyl-glycero-3-phosphocholine)

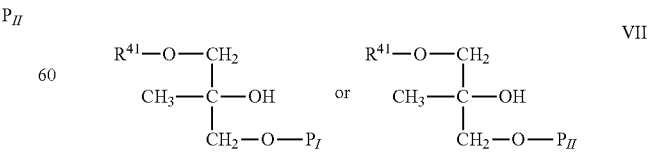

VII wherein $R^{41}$ is a saturated or singly or multiply unsaturated hydrocarbon radical containing 15 to 26 carbon atoms, wherein $P_I$ and $P_{II}$ have the above-indicated meanings, characterised in that the composition further contains the constituent b) comprising cholesterol, 7 β-hydroxycholesterol and/or a β-sitosterol and also as a constituent c) a negative charge carrier selected from
a carboxylic acid which contains from 16 to 36 carbon atoms, is preferably a saturated, singly unsaturated and multiply unsaturated fatty acid and particularly preferably contains cis double bonds,
or a compound from the natural substance class of the bile acids,
or fatty acid amides of amino acids containing fatty acids which can be saturated, singly or multiply unsaturated,
or a compound of general formula VIII (fatty acid amides of GPE)

VIII

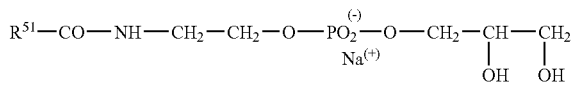

wherein $R^{51}$ is a hydrocarbon radical containing 15 to 25 carbon atoms.

According to the invention, it has been found that the purposeful selection of specific negative charge carriers allows pharmaceutical preparations and, in particular, liposomes having outstanding properties to be obtained. The negative charge carrier used is preferably a carboxylic acid, in particular a fatty acid, containing 16 to 36 carbon atoms, more preferably containing 16 to 24 and most preferably containing 16 to 22 carbon atoms. The carboxylic acid can be linear or branched and saturated or singly or multiply unsaturated. Preferred are multiply unsaturated fatty acids containing cis double bonds. Particularly preferred are, oleic acid, linoleic acid, erucic acid or retinoic acid. Bile acids also have a carboxyl group. Representatives of the bile acids preferably used include cholic acid, deoxycholic acid, lithocholic acid, chenodeoxycholic acid, 24-cholanic acid and also ursodeoxycholic acid.

The carboxylic acids used in accordance with the invention as a negative charge carrier are distinguished by their easy availability and cost-effectiveness.

In a preferred and inexpensive alternative, use is made of a combination of acids which was obtained by hydrolysis from olive oil and contains approx. 85% oleic acid, 10% linoleic acid and the remaining 5% being further fatty acids. However, the fatty acids are of secondary importance for the pricing of the formulation, as fatty acids form <10% of the overall formulation. However, as a starting product for the synthesis of the active ingredient oleylphosphocholine, olive oil is an interesting alternative to the use of pure oleic acid as the starting product.

Especially good results are achieved if use is made of a substantially deprotonated carboxylic acid, for example a carboxylic acid that is more than 50%, more preferably more than 70%, even more preferably more than 90% and most preferably more than 95% deprotonated. The deprotonation can be achieved by adjusting the pH, for example by the addition of lye to carboxylic acid solutions. On addition of sodium hydroxide solution to carboxylic acids, the sodium salts of the carboxylic acids for example are formed.

If carboxylic acids having a pH of approximately 5 are used, an advantageous buffer effect is additionally obtained. As numerous carboxylic acids, such as for example oleic acid, are also stable in heat, heat-sterilisable pharmaceutical preparations according to the invention and, in particular, heat-sterilisable liposomes can be obtained.

Fatty acid amides of amino acids are also preferably used as the negative charge carrier. Here too, the deprotonatable group is a carboxyl group. The natural amino acids such as, for example, glycine, sarkosine, alanine, serine, etc., are preferably used as the amino acid. The fatty acid content of the fatty acid amides preferably originates from unsaturated or singly or multiply unsaturated fatty acids ($C_{16}$ to $C_{36}$), more preferably from fatty acids having a cis double bond.

It has also been found that further negative charge carriers suitable for the formation of liposomes can be obtained starting from glycerophosphoethanolamine (G-PE) which is a by-product of soya preparation. A fatty acid can be introduced to the glycerophosphoethanolamine using an amide bond. Blocking of the otherwise positively charged amino group thus provides an overall negatively charged molecule which is suitable as a negative charge carrier. A fundamental difference from the above-described negative charge carriers, which are all based on the deprotonation of a carboxyl group (pK 5 to 6), resides in this case in the use of a phosphate group as a negative charge carrier having pKs of about 2.

The radical $R^{51}$ in compounds of formula VIII is a saturated or a singly or multiply unsaturated radical preferably containing cis double bonds.

Preferred active ingredients are compounds of formula I in which $R^1$ is a singly unsaturated hydrocarbon containing 15 to 26 carbon atoms such as, for example, oleyl or erucyl containing a respective cis double bond, wherein n=2 or n=3, but also containing the saturated radical hexadecyl. For compounds of formula II, a preferred use of $R^1$ is also as a singly unsaturated hydrocarbon containing 15 to 26 carbon atoms such as, for example, oleyl or erucyl containing a respective cis double bond, wherein n=2 or n=3, but also containing the saturated radical octadecyl.

a), b) and c) preferably together form 100 mol %. However, a water-miscible, physiologically acceptable alcohol containing 2 to 4 carbon atoms and optionally containing water and also optionally conventional pharmaceutical auxiliaries and/or active ingredients can also be added to the formulation. The components are preferably provided as complexes dispersed in water in the form of liposomes which conventionally have a diameter of from 70 to 150 nm, i.e. can easily still be filtered under sterile conditions. However, even more important is that the formulations can be heat-sterilised and stored at 20° C. These "liposomes" are formed in water by mild ultrasonic treatment. No high-pressure homogenisers are therefore required for the preparation.

It has surprisingly been found that the packing of the active ingredients in the liposomes according to the invention has considerable advantages over free active ingredients. Packing in the liposomes allows, in particular, an increase in the desired efficacy and at the same time a reduction in undesirable side effects to be achieved. Haemolytic activity is thus markedly reduced on administration in liposomal form, as could be demonstrated in a haemolysis test.

The cholesterol, 7-β-hydroxycholesterol or β-sitosterol also enclosed in the liposomes inhibits the haemolytic activity of the alkylphosphocholines, i.e. the active ingredient compounds. This allows the active ingredients to be used and applied in much higher concentrations. Whereas the free active ingredients irritate the tissue and lead to sores at concentrations as low as about $10^{-4}$ M, in liposomal form concentrations of these active ingredients of >60 mM can be used. Any form of application is possible, such as for example intravenous, intramuscular, subcutaneous, etc. up to oral or topical application.

It is noteworthy that the liposomal formulations proposed in this case have marked advantages over the free active ingredients, alkylphosphocholines in physiological saline solution, even when administered orally. In relatively high concentrations of the free alkylphosphocholines, there is observed in rats as test animals major irritation of the gastrointestinal tract associated with a loss of appetite leading to considerable loss in weight, of up to 30% within a period of three weeks. Tests using corresponding amounts of alkylphosphocholines in the form of liposomal formulations are entirely straightforward. The animals do not display any noteworthy characteristics, and no weight loss is observed. Oral treatment with liposomal alkylphosphocholines is therefore greatly superior to treatment with free active ingredients.

In the prior art, use was frequently made of auxiliaries which were pharmacologically novel and the toxicity of which was unknown—a problem that is said to have led not only to the costs associated with establishing the safeness of these substances but also to considerable time delays. The stability in storage at 20° C. of the liposomal dispersions provided for this purpose was also of considerable importance, as these pharmaceutical compositions are frequently used in Southern countries. The formulation should, if possible, also be heat-sterilisable to obtain a release of the pharmaceutical composition over a period of three years. All of these prerequisites, which are almost obligatory for use in veterinary medicine, could be adhered to for the liposomal formulations proposed in the present case.

The invention is based on the fact that the active ingredients specified under formulae I to VII are easily introduced as integral constituents of liposomes—together with cholesterol, 7-β-hydroxycholesterol or β-sitosterol and a negative charge carrier. The active ingredients can be prepared cost-effectively. Cholesterol and β-sitosterol can be purchased inexpensively, as can most negative charge carriers.

Also of major importance is the simple and cost-effective preparation of the liposomes, their heat-sterilisability and capacity to be stored at 20° C. There are thus provided liposomal formulations of active ingredients that can be used in the aforementioned life-threatening diseases substantially without side effects.

The pharmaceutical preparations according to the invention can contain as an active ingredient a phospholipid compound, in particular an alkylphosphocholine compound.

In component a), the phospholipid or alkylphosphocholine of formula I, the hydrocarbon radical $R^1$ can contain 16 to 26 carbon atoms, 16 to 24 carbon atoms being particularly preferred and 18 to 22 carbon atoms even more preferred. Particularly preferably, $R^1$ is an alkyl radical or a singly or multiply unsaturated alkenyl radical and, in particular, a hexadecyl, heptadecyl, octadecyl, nonadecyl, eicosyl, hexadecenyl, heptadecenyl, octadecenyl (oleyl), nonadecenyl, eicosenyl, elaidyl, eicosenyl-cis (w-9), heneicosyl, heneicosenyl, docosyl, docosenyl, linoleyl, linolenyl, erucyl or tetracosadienyl radical. The hydrocarbon radical can be saturated or singly or multiply unsaturated, but in particular singly or doubly unsaturated, the double bond(s) of the unsaturated radicals particularly preferably being in the cis position. If there is more than one cis double bond, they are preferably not conjugated. The hydrocarbon radical can be branched or linear but is preferably linear.

For the treatment of leishmaniasis, compounds containing cis double bonds such as, for example, nonadecenyl, eicosenyl, heneicosenyl and oleyl are particularly preferred. Most preferred, however, is the compound of formula I wherein $R^1$=oleyl and n=2, i.e. oleylphosphocholine.

For the treatment of cancer, the compounds containing a cis double bond such as, for example, oleyl and erucyl are particularly preferred. Most preferred are two compounds of formula I, a) wherein $R^1$=erucyl and n=2, i.e. erucylphosphocholine, and b) wherein $R^1$=erucyl and n=3, i.e. erucyl-phospho-(N,N,N)-trimethyl-propylammonium. Compounds containing an unsaturated radical $R^1$ have the advantage of having both a broad therapeutic scope and low toxicity, such as for example oleylphosphocholine, erucylphosphocholine and erucylphospho-(N,N,-trimethyl)-propylammonium.

In formula I, $R^2$, $R^3$ and $R^4$ are each preferably methyl. Examples of other suitable radicals include ethyl, propyl, butyl and pentyl radicals, cyclopropyl, cyclobutyl, cyclopentyl and cyclohexyl radicals, hydroxyethyl and hydroxypropyl radicals. Two of the radicals $R^2$, $R^3$ and $R^4$ can, for example, form a pyrrolidine, a piperidine or a morpholine group. Preferably, at least one of the radicals $R^2$, $R^3$ and $R^4$ is different from hydrogen; particularly preferably, all three radicals are different from hydrogen.

The polar constituent of the compounds of formula I consists preferably of phosphocholine (PC), i.e. n is particularly preferably equal to 2–n can preferably also be 3 or 4. A leukopoesis-stimulating effect was surprisingly found, especially in compounds wherein n is equal to 3.

Alkylphosphocholines that are suitable and can be used as constituent a) are, for example, the compounds described in EP 0 507 337 or WP 00/08031.

In the phospholipid compounds, in particular in those containing short hydrocarbon chains in the radical $R^1$, a harmful haemolytic effect often occurs in conventional formulations. This effect is markedly reduced by the combination according to the invention. In short-chain radicals $R^1$ with hydrocarbon radicals containing 15 to 21 carbon atoms, cholesterol or cholesterol derivatives or β-sitosterols in the above-indicated quantitative range are therefore preferred. It is therefore preferred to have a small excess of cholesterol or the derivative thereof in the complex or liposome, so the molar ratio between the compound of formula I and cholesterol/cholesterol derivative is preferably 1:1 to 1.2. For compositions according to the invention, in which the active ingredient used as constituent a) comprises a radical R containing ≤21 carbon atoms, the mixing ratio is preferably from 30 to 45 mol % constituent a), 30 to 60 mol % constituent b) (cholesterol) and 3 to 30 mol % constituent c), i.e. negative charge carriers such as fatty acids, etc.

In compounds comprising a radical $R^1$ having relatively long hydrocarbon chains containing 22 to 26, in particular up to 24 carbon atoms, the problem is less that of haemolysis than that of low water solubility. For this reason, a molar ratio of phospholipid compound: cholesterol/cholesterol derivative of preferably 1:0.5 to 1 is sufficient in this case.

For compositions according to the invention in which the active ingredient of component a) used is a compound containing $R^1$≥22 carbon atoms, the mixing ratio of the individual components is preferably from 30 to 55 mol % component a), 10 to 40 mol % component b) (cholesterol) and 3 to 30 mol % component c), i.e. negative charge carriers such as fatty acids, etc.

The conditions for good antineoplastic efficacy, in particular half-lives in organs and tissues from 60 to 100 hours, can be achieved by the above-specified active ingredients.

Very generally, it can be stated that the compounds of formulae I to VII have very similar physical properties and can be compared with lysolecithins. These molecules have in common a long alkyl chain which can be linked directly to phosphocholine (formula PI) or an analogue (formula $P_n$), as in the case of the alkylphosphocholines. However, the linking can also be carried out via a diol bridge, for example in formula III via ethylene glycol, in formula IV via alkanediol (1,2), in formula V via glycerol, in formula VI via propanediol-(1,3), in formula VII via 2-methylglycerol.

Physically, in terms of their haemolytic and cytolytic properties, these molecules are very similar to lysolecithins as substances inherent in the body; the critical micelle concentrations are also comparable if the length of the alkyl chains remains unchanged. Biologically, however, there are enormous differences. The half-life of lysolecithins in biological cells and organs is short, <1 min. Lysolecithins are metabolised quickly, i.e. converted into lecithins by acylation via acyltransferases. This reacylation is not possible in the molecules of formulae I to VI—prevented because the free secondary hydroxyl group is missing or already blocked in the lysolecithin (see formula V). A special situation is encountered in formula VII in which a hydroxyl function is in position 2. However, this is a tertiary hydroxyl group that cannot be acylated by acyltransferases. In contrast to lysolecithins, the compounds of formulae I to VII therefore have long biological half-lives of from 60 to 100 hours.

The pharmaceutical preparations according to the invention can contain as an active ingredient, in addition to the alkylphosphocholines of formula I discussed in detail hereinbefore, compounds of formulae II to VII. The preferred meanings discussed hereinbefore for $R^1$ similarly apply to the radicals $R^{11}$, $R^{21}$, $R^{31}$ and $R^{41}$. The above-mentioned major similarities in the physical properties are so extensive that the protective function of the cholesterol, the β-hydroxycholesterol and the β-sitosterol, in particular the function of providing protection against haemolysis and cytolysis, is also maintained for all of the aforementioned substances under formulae II to VII. The radicals discussed in detail for the alkylphosphocholines of the formulae are also the corresponding preferred radicals in the substances of formulae II to VII.

In the alkylphosphocholine-like compounds of formula II to VII, the hydrocarbon radical $R^{11}$, $R^{21}$, $R^{31}$ or $R^{41}$ can contain 16 to 26 carbon atoms, 16 to 22 carbon atoms being particularly preferred, 18 to 22 carbon atoms being more particularly preferred. Particularly preferably, at least one cis double bond is present in the molecule. Particularly preferably, $R^{11}$, $R^{21}$, $R^{31}$ or $R^{41}$ is an alkyl radical, an alkenyl radical, an alkadienyl radical or an alkatrienyl radical and is in particular a hexadecyl, heptadecyl, octadecyl, nonadecyl, eicosyl, hexadecenyl, heptadecenyl, octadecenyl(oleyl), linolyl, linolenyl, nonadecenyl, eicosenyl, elaidyl, eicosenyl-cis-(w-9), heneicosyl, heneicosenyl, docosyl or docosenyl radical. The hydrocarbon radical can be saturated or singly or multiply unsaturated, but in particular singly or double unsaturated, the double bond(s) of the unsaturated radicals preferably being in the cis position. If there is more than one cis double bond, they are preferably not conjugated. The hydrocarbon radical can be branched or linear and is preferably linear.

For the treatment of leishmaniasis, compounds containing cis double bonds such, for example, nonadecenyl, eicosenyl, heneicosenyl, and oleyl are particularly preferred. Most preferred are the compounds of formulae II to VII wherein $R^{11}$, $R^{21}$, $R^{31}$ or $R^{41}$=oleyl and n=2, i.e. for formula II: oleyl-ethylene glycol-phospho-(N,N-dimethyl)-pyrrolidinium; for formula III: oleyl-ethylene glycol-phosphocholine (version PI) or oleyl-ethylene glycol-phospho-(N,N-dimethyl)-pyrrolidinium (version $P_{II}$); for formula IV: 1-oleyl-propanediol-(1,2)-phosphocholine (version $P_I$) or 1-oleyl-propanediol-(1,2)-phospho-(N,N-dimethyl-pyrrolidinium (version $P_{II}$); for formula V: 1-oleyl-2-methyl-glycero-3-phosphocholine (version $P_I$) or 1-oleyl-2-methyl-glycero-3-phospho-(N,N-dimethyl)-pyrrolidinium (version $P_{II}$) including all stereoisomers and configurational isomers; for formula VI: oleyl-2,2-dimethyl-propanediol-(1,3)-phosphocholine (version $P_I$) or oleyl-2,2-dimethyl-propanediol-(1,3)-phospho-(N,N-dimethyl)-pyrrolidinium (version $P_{II}$); for formula VII: 1-oleyl-2-methyl-propanetriol-phosphocholine (version $P_I$) or 1-oleyl-2-methyl-propanetriol-phospho-(N,N-dimethyl)-pyrrolidinium.

For the treatment of cancer, the corresponding compounds containing oleyl and erucyl are particularly preferred, again containing a respective cis double bond. Most preferred, however, are all compounds of formulae II to VII carrying in $R^{11}$, $R^{21}$, $R^{31}$ or $R^{41}$ an erucyl radical, for example for formula II: erucyl-phospho-(N,N-trimethyl)-pyrrolidinium; for formula III: erucyl-ethylene glycol-phosphocholine (version $P_I$, n=2) or erucyl-ethylene glycol-phospho-(N,N,N-trimethyl)-propylammonium (version $P_I$, n=3); or for formula IV: erucyl-propanediol-(1,2)-phosphocholine (version $P_I$, n=2) or erucyl-propane diol-(1,2)-phospho-(N,N,N-trimethyl)-propylammonium (version $P_I$, n=3), or for formula V: 1-erucyl-2-methyl-glycero-3-phosphocholine (version $P_I$, n=2) or 1-erucyl-2-phospho-(N,N,N-trimethyl)-propylammonium (version $P_I$, n=3); or for formula VI: erucyl-2,2-dimethyl-propanediol-(1,3)-phosphocholine (version $P_I$, n=2) or erucyl-2,2-dimethyl-propanediol-1,3-phospho-(N,N,N-trimethyl)-propylammonium (version $P_I$, n=3); or for formula VII: ercucyl-2-methyl-propanetriol-phosphocholine (version $P_I$, n=2) or erucyl-2-methyl-propanetriol-phospho-(N,N,N-trimethyl)-propyl-ammonium.

Particularly preferred are hexadecyl, octadecyl and oleyl. Most preferred is a compound of formula I, wherein $R^1$=oleyl, in particular a cis oleyl radical. Further preferred radicals $R^1$ include linoleyl, linolenyl and erucyl radicals.

Compounds containing an unsaturated radical $R^{11}$, $R^{21}$, $R^{31}$ or $R^{41}$ have the advantage of having both a broad therapeutic scope and low toxicity. Compared to compounds containing saturated radicals, this allows higher doses.

$R^2$, $R^3$ and $R^4$ are preferably methyl, ethyl or propyl.

In the embodiment containing $P_I$ and $R^2$, $R^3$ and $R^4$, these radicals are preferably each methyl. Examples of other suitable radicals include ethyl, propyl, butyl and pentyl radicals, cyclopropyl, cyclobutyl, cyclopentyl and cyclohexyl radicals, hydroxymethyl, hydroxyethyl and hydroxypropyl radicals. Two of the radicals $R^2$, $R^3$ and $R^4$ can form, for example, a pyrrolidine, a piperidine or a morpholine group.

The amount of active ingredient of formulae I to VII in the pharmaceutical preparations according to the invention is from 10 to 60 mol %, preferably at least 20 mol %, in particular at least 25 mol %, more preferably at least 40 mol % up to preferably 50 mol %, in particular up to 45 mol %.

As a further constituent, the liposomes according to the invention contain cholesterol or sitosterol. The term "cholesterol", as used in the present document, refers to both cholesterol itself and cholesterol derivatives, for example 7-β-hydroxycholesterol.

Instead of or in addition to cholesterol, a β-sitosterol can also be contained as component b). β-sitosterols are plant steroids that, in certain partial ranges, are very similar to cholesterol and conventionally contain one or two methyl groups more than cholesterol. It is thus possible to prepare cholesterol-free liposomes. Pharmaceutical preparations of this type are especially advantageous in patients having cholesterol level problems, as they do not raise the cholesterol level and can also be prepared exclusively from vegetable starting materials. β-sitosterol has even gained some recognition as an important means for lowering the cholesterol level. The amount of cholesterol or β-sitosterol is from 10 to 60 mol %, preferably 25 to 50 mol %, in particular 30 to 40 mol %.

Component c) of the liposomes according to the invention is a negative charge carrier, as discussed hereinbefore. $R^a$ and $R^{10}$ are preferably a hydrocarbon radical containing 16 to 22 carbon atoms. Preferably, the amount of constituent c) is from 5 to 15 mol %, in particular 7 to 10 mol %.

In a preferred embodiment, the pharmaceutical preparation according to the invention contains as an active ingredient a) a compound wherein $R^1$, $R^{11}$, $R^{21}$, $R^{31}$ or $R^{41}$ is a saturated or unsaturated hydrocarbon radical containing 16 to 26 carbon atoms and as constituent c) as the negative charge carrier, a carboxylic acid containing 16 to 36 carbon atoms. Particularly preferably, these two components are chosen so that the radical $R^1$, $R^{11}$, $R^{21}$, $R^{31}$, or $R^{41}$ corresponds precisely to the carboxylic acid radical of constituent c); for example, an oleyl radical is used for $R^1$ etc. and oleic acid as the negative charge carrier.

It has surprisingly been found that using the above-mentioned negative charge carriers provides liposomes which are stable to heat and can therefore be heat-sterilised. This is a considerable advantage over other liposome formulations, in particular with regard to a possible intravenous or subcutaneous administration of the liposomes. Liposomes of this type are therefore preferably heat-sterilised after the formation thereof and prior to administration.

The pharmaceutical preparations according to the invention, in particular in the form of liposomes, also have high stability and a long storage capacity. Thus, in the formulations according to the invention, all of the constituents, including the negative charge carrier, are stable in water. No decomposition is observed even in extreme pH ranges of pH 1 to pH 11. The formulations also have high stability with respect to oxygen. The stability in storage of the pharmaceutical preparations according to the invention even at high ambient temperatures is a crucial advantage, in particular, for use in hot countries, the diseases discussed in the present document often being a major problem specifically in hot Southern countries. The high stability in storage is also very useful to vets, as these required medicines often have to be stored for relatively long periods of time.

Preferably, the pharmaceutical formulation contains the constituents in an amount such that it has overall a negative excess charge. This is especially advantageous when using active ingredients containing relatively long hydrocarbon chains. The problem of poor water solubility in compounds containing relatively long chains, such as for example $C_{22}$, is especially important on intravenous administration; an oral application, on the other hand, is not beneficial as <10% are resorbed.

The molar ratio of the individual constituents of the liposomes according to the invention can vary so, for example, active ingredients of formulae I to VII are present in a slight deficit. Generally preferred, however, is a ratio that does not deviate excessively from 1:1, for example for a molar ratio of an active ingredient of formulae I to VII to cholesterol or β-sitosterol of from 1:1.2 to 1:1. The liposome preferably contains from 45 to 55 mol % cholesterol or β-sitosterol.

The liposome-like complex formed from constituents a), b) and c) can easily be filtered under sterile conditions through membranes having a pore diameter of 0.8µ, 0.45µ and even 0.2µ. This is a considerable advantage over conventional liposomes which are not easy to filter under sterile conditions. More important, however, is the fact that the liposomes can be heat-sterilised. It has also surprisingly been found that liposomes according to the invention are extremely stable in storage.

Components a, b and c preferably together form 100% of the liposomes according to the invention. However, it is also possible to form liposomes containing further envelope constituents and/or encapsulated substances. Preferred are liposomes comprising further active ingredients in encapsulated form. Additional active ingredients that can advantageously been contained in the liposomes according to the invention include, for example, oxytetracycline, doxycycline or minocycline which are effective as bactericides; Amphotericin B or griseofulvin which are effective fungicides and also cyclosporine which acts as an immunosuppressive and arthemeter and related substances which are effective against malaria.

Instead of diluting using aqueous liquids, it is also possible to prepare the pharmaceutical formulation according to the invention in a different form, for example as powders, tablets, capsules or else as an ointment. In this case, the alcohol is preferably added in a smaller amount than in the preparation of the formulation for use in liquid form. Preferred in this case is a phospholipid compound to alcohol molar mixture ratio of from 1:5 to 100. Optionally, the alcohol can be at least partially removed again from the mixture in order to obtain a concentrated formulation. For this purpose the pharmaceutical formulation can be mixed with conventional physiologically acceptable fillers, excipients, diluting agents and/or auxiliaries and, for example, poured out in hollow cells of corresponding size or introduced or granulated in capsules of corresponding size and then compressed to form tablets, optionally with the addition of further conventional auxiliaries. The formulation can be mixed, for example, with one or more of the following auxiliaries: starch, cellulose, lactose, formalin, casein, modified starch, magnesium stearate, calcium hydrogen phosphate, highly disperse silica, talc and phenoxyethanol. The obtained mixture can optionally be granulated with an aqueous solution of, for example, gelatin, starch, polyvinylpyrrolidone, vinylpyrrolidone/vinyl acetate copolymer and/or polyoxyethylene sorbitate monooleate and then be compressed to form tablets or introduced in capsules.

An embodiment, having particularly few side effects, of these active ingredients in the form of tablets, capsules, etc. is the use of the active ingredients in combination with cholesterol, β-sitosterole or other cholesterol analogues in the molar ratios described for the liposomes.

The pharmaceutical preparations according to the invention can be used, in particular, for the treatment and/or prophylaxis of protozoan diseases. It has been found that the liposomal preparations are outstandingly effective against protozoan diseases and diseases caused thereby and are especially effective against plasmodia and thus for the treatment or prophylaxis of malaria, against trypanosomes and thus for the treatment or prophylaxis of sleeping sickness, against amoebae, for example endamoebae and acanthamoebae, for the treatment or prophylaxis of amoebiasis and encephalitis and, in particular, against *leishmania* and thus for the treatment or prophylaxis of leishmaniasis. In addition to the treatment of humans, the pharmaceutical preparations according to the invention can advantageously also be used in the treatment of animals, in particular in leishmaniasis in dogs. Particularly preferably, the pharmaceutical formulations are used for the treatment of leishmaniasis and/or for the treatment of diseases caused by amoebae. In the treatment of leishmaniasis, use is preferably made of formulations containing Amphotericin B as an additional active ingredient.

It has also been found that the pharmaceutical formulations according to the invention are outstanding antitumour agents. They can thus be used for the treatment and/or prophylaxis of cancer, in particular of leukaemia and solid tumours. The substances have also proven highly successful in the treatment of cancer in dogs. Thus, for example, Cushing's and bladder tumours could be treated successfully with erucylphospho-(N,N,N-trimethyl)-propylammonium.

They can also be used for the stimulation of leukopoesis and for the treatment of diseases caused by arthropods and of acarinosis.

It has surprisingly been found that the pharmaceutical formulations according to the invention are also highly effective against acarinosis, in particular scabies, and against diseases caused by arthropods and by ascarids, such as for example acarines or ticks.

Additional active ingredients can, if desired, promote, supplement or extend these indications. An addition of Amphotericin B, in particular, displayed synergistic enhancement of efficacy against protozoan diseases and extension to systemic mycoses.

The pharmaceutical formulations according to the invention are also outstandingly effective against bacterial diseases. They can therefore also be used for the treatment and/or prophylaxis of bacterial diseases, in particular for the treatment and/or prophylaxis of ehrlichiosis. Ehrlichiosis is a bacterial disease transmitted by ticks. In the treatment of dogs with pharmaceutical formulations according to the invention, not only was a marked reduction in the ehrlichiosis titre observed, a cure was achieved. The treatment of ehrlichiosis can also be carried out in combination with tetracyclines.

Ocular diseases associated with cellular proliferations such as, for example, proliferative vitreoretinopathy or detachment of the retina from the eye, which are difficult to treat operatively and are also often associated with very markedly proliferating cells, can also successfully be treated or prevented using the pharmaceutical preparations according to the invention.

The treatment of the aforementioned diseases can be carried out almost without side effects. Surprisingly, the use of the pharmaceutical formulations according to the invention does not lead to the immunosupression feared in chemotherapy but rather even to stimulation of leukopoesis. The blood count is also normalised over the course of the treatment. In other words, the formulations described in the present document comprising alkylphosphocholines as an active ingredient are ideal for long-term treatments and allow side effect-free treatment in therapeutically effective doses. The alkylphosphocholines especially emphasised in the present document are ones comprising at least one cis double bond in the molecule such as, for example, oleylphosphocholine, erucylphosphocholine or erucylphospho-(N,N,N-trimethyl)-propylammonium. Alkylphosphocholines containing cis double bonds are distinguished by a substantially broader therapeutic scope, i.e. much higher doses can be applied than in saturated alkylphosphocholines. This is especially advantageous if erufosin treatment is combined with radiation therapy. Tumour cells doped with erufosin are sensitised to radiation therapy and particularly susceptible.

In combination with cyclosporin A, in particular, the preparations can also be used for immunosupression.

The pharmaceutical preparations according to the invention, in particular in the form of liposomes, are preferably used for the treatment of mammals and most preferably for the treatment of dogs or humans.

It has surprisingly been found that the pharmaceutical preparations according to the invention are ideal for the purposes of treatment and/or prophylaxis carried out on animals, in particular in the case of dogs. Accordingly, the pharmaceutical preparations according to the invention are preferably used in veterinary medicine, in particular for the treatment of tumour and protozoan diseases. Especially in dogs, in which previous compositions suitable for humans have often failed, outstanding results could be obtained using the compositions according to the invention. Thus, for example, leishmaniases and ehrlichioses in animals, in particular in dogs, can be successfully treated using the pharmaceutical preparations according to the invention. Particularly preferably, in this regard, oleylphosphocholine is used as an active ingredient and oleic acid as a negative charge carrier.

It has also been found that the formulations according to the invention can also be used successfully to treat ocular diseases, in particular ocular diseases associated with uncontrolled cellular processes.

The present invention relates to novel pharmaceutical formulations containing as active ingredients alkylphosphocholines and analogues, alkyl-alkanediol-phosphocholines and analogues and also (ether)lysolecithins and analogues in various embodiments. The active ingredients are in this case integral constituents of liposomes also containing cholesterol and analogues and also a negative charge carrier.

The pharmaceutical formulations are especially suitable for the treatment and/or prophylaxis of cancer, of protozoan diseases such as leishmaniasis and amoebic diseases, of acariasis and of diseases caused by arthropods and also of bacterial diseases such as, for example, ehrlichiosis. Ocular diseases associated with uncontrolled cellular processes can also be beneficially influenced.

The following examples will serve to illustrate the invention.

EXAMPLES

Example Group 1

Variation of the Oleylphosphocholine/Cholesterol Ratio

| | |
|---|---|
| Oleylphosphocholine | (MG 433.61)(Ol-PC) |
| Cholesterol | (MG 386.66)(Chol) |
| Oleic acid | (MG 282.47) |
| NaOH | (MG 40.00) |

Example 1 (a)

Ol-PC, 40 mM; Chol 35 mM

| | | |
|---|---|---|
| Ol-PC | 40.0 mM; 1.73 g | |
| Chol | 35.0 mM; 1.35 g | weighed-in portion: 100 g = 100 ml |
| Oleic acid | 10.0 mM; 0.283 g | |
| NaOH | 9.5 mM; 9.50 g 0.1 N NaOH | |

Preparation

The weighed-in portion was dissolved in 30 ml $CH_2Cl_2$, $CH_2Cl_2$ was removed, dried to a constant weight, mixed with 50 g 0.3 M 1,2-propanediol and 9.5 g 0.1 N NaOH and sufficient 0.3 M 1,2-propanediol was added to make the overall weight 100 g.
a) annealing at 55° C. for 10 min
b) ultrasound (100%) at 55° C. for 20 min
0.2μ of the mixture was filtered when still warm and stored at from +4° C. to +8° C.
Observations—stable, at least 1 year at from +4° C. to +8° C.

Example 1 (b)

Ol-PC, 40 mM; Chol 40 mM

| | | |
|---|---|---|
| Ol-PC | 40.0 mM; 1.73 g | |
| Chol | 40.0 mM; 1.55 g | weighed-in portion: 100 g = 100 ml |
| Oleic acid | 10.0 mM; 0.283 g | |
| NaOH | 9.5 mM; 9.50 g 0.1 N NaOH | |

Preparation—as in Example 1 (a)
Observations—stable, at least 1 year at from +4° C. to +8° C.

Example 1 (c)

Ol-PC, 40 mM: Chol 45 mM

| | | |
|---|---|---|
| Ol-PC | 40.0 mM; 1.73 g | |
| Chol | 45.0 mM; 1.74 g | weighed-in portion: 100 g = 100 ml |
| Oleic acid | 10.0 mM; 0.283 g | |
| NaOH | 9.5 mM; 9.50 g 0.1 N NaOH | |

Preparation—as in Example 1 (a)
Observations—stable, at least 1 year at from +4° C. to +8° C.

According to the results obtained in Examples 1 (a) to 1 (c), a preparation for the subcutaneous treatment of dogs can have the following composition:

| | | mM |
|---|---|---|
| Ol-PC | (active ingredient) | 35-45 |
| Chol | (auxiliary) | 35-45 |
| Oleic acid | (95%) | 8-12 |

Example Group 2

Variation of the Oleic Acid Content

The composition was varied with regard to the oleic acid content, although in all cases at a degree of protonation of 95%. These variations were examined on

| | |
|---|---|
| Ol-PC | 40.0 mM |
| Chol | 40.0 mM |

Oleic acid as sodium salt was varied between 2.0 mM and 25 mM. Some easy-to-use storable formulations are described precisely under 2 (a) to 2 (d).

| | |
|---|---|
| Oleylphosphocholine | (MG 433.61), |
| Cholesterol | (MG 386.66) |
| Oleic acid | (MG 282.47) |
| NaOH | (MG 40.00) |

Example 2 (a)

Ol-PC, 40 mM; Chol 40 mM; oleic acid 16 mM

| | | |
|---|---|---|
| Ol-PC | 40.0 mM; 1.73 g | |
| Chol | 40.0 mM; 1.55 g | weighed-in portion: 100 g = 100 ml |
| Oleic acid | 16.0 mM; 0.452 g | |
| NaOH | 15.2 mM; 7.60 g 0.1N NaOH | |

Preparation—as in Example 1 (a)
Observations—stable, at least for 1 year at from +4° C. to +8° C.; does not irritate tissue in dogs.

Example 2 (c)

Ol=PC, 40 nM; Chol 40 mM; oleic acid 8 mM

| | | |
|---|---|---|
| Ol-PC | 40.0 mM; 1.73 g | |
| Chol | 40.0 mM; 1.55 g | weighed-in portion 100 g = 100 ml |
| Oleic acid | 8.0 mM; 0.225 g | |
| NaOH | 7.6 mM; 7.60 g 0.1N NaOH | |

Preparation—as in Example 1 (a)
Observations—stable, for at least 1 year at from +4° C. to +8° C.; does not irritate tissue in dogs.

Example 2 (c)

Ol-PC, 40 mM; Chol 40 mM; oleic acid 6 mM

| | | |
|---|---|---|
| Ol-PC | 40.0 mM; 1.73 g | |
| Chol | 40.0 mM; 1.55 g | weighed-in portion 100 g = 100 ml |
| Oleic acid | 6.0 mM; 0.170 g | |
| NaOH | 5.6 mM; 5.60 g 0.1N NaOH | |

Preparation—as in Example 1 (a)
Observations—stable, at least for 1 year at from +4° C. to +8° C.; does not irritate tissue in dogs.

Example 2 (d) Ol-PC, 40 mM; Chol 40 mM; oleic acid 4 mM

| | | |
|---|---|---|
| Ol-PC | 40.0 mM; 1.73 g | |
| Chol | 40.0 mM; 1.55 g | weighed-in portion: 100 g = 100 ml |
| Oleic acid | 4.0 mM; 0.112 g | |
| NaOH | 3.8 mM; 3.80 g 0.1N NaOH | |

Preparation—as in Example 1 (a)
Observations—stable, at least for 1 year at from +4° C. to +8° C.; does not irritate tissue in dogs.

Example Group 3

Preparation of Ol-PC Dispersions for Application in Tests on Animals

| | |
|---|---|
| Oleylphosphocholines (MG 433.61) | 39.20 mM |
| Cholesterol (MG 386.66) | 41.40 mM |
| Oleic acid (MG 282.47) | 5.66 mM |
| NaOH (MG 40.00) | 5.40 mM |

Weighed-In Portion

|  | Per 1 kg | Per 0.5 kg | Per 0.1 kg |
|---|---|---|---|
| Ol-PC | 17.00 g | 8.5 g | 1.700 g |
| Chol | 16.00 g | 8.0 g | 1.600 g |
| Oleic acid | 1.60 g | 0.8 g | 0.160 g |
| NaOH, 0.1 N | 54.00 g | 27.0 g | 5.400 g |

Example 3 (a)

Preparation of a Sample Dispersion of 100 g Ol-PC

The amounts of substance required for 0.1 l=100 ml were weighed out into a 500 ml round-bottom flask and completely dissolved in 40 ml $CH_2Cl_2$. The solution had to be clear and free from particles. $CH_2Cl_2$ was removed on a rotary evaporator under a slight vacuum and the residue was dried under vacuum to a constant weight, most simply overnight. Result: 3.44 to 3.46 g corresponding to >99% of the weighed-in portion.

The residue was mixed with a solution consisting of 90 ml 0.289 M 1,2-propanediol and 5.4 ml 0.1 M NaOH and the overall weight was brought to 100 g. The error in volume occurring in this case with 0.289 M 1,2-propanediol was low, as the density of the dispersion corresponded to approximately 1. The mixture was heated to 55° C. with rotation and the system kept at this temperature:
a) annealing at 55° C. for 10 min
b) ultrasound (100%) at 55° C. for 20 min The mixture was sterile-filtered while still warm through 0.2μ and stored at from +4° C. to +8° C.
Observations—the dispersion is stable, storage at least 1 year.
It meets all important criteria.
Stability in storage
Filtration under sterile conditions possible
Heat sterilisation possible
Synthesis for auxiliary dispensed with
Auxiliary pharmaceutically known
Auxiliary also has a buffer capacity at pH 5.0

Example 3 (b)

Preparation of a Dispersion of 500 g Ol-PC

The amounts of substance required for 0.5 l=500 ml were weighed out in a 1 l round-bottom flask and completely dissolved in 100 ml $CH_2Cl_2$. The solution has to be clear and free from particles. $CH_2Cl_2$ was removed on a rotary evaporator under a slight vacuum and the residue was dried to a constant weight, most simply under vacuum overnight. Result: 17.2 to 17.3 g, corresponding to >99% of the weighed-in portion.

The residue was mixed with a solution consisting of 450 ml 0.289 M 1,2-propanediol and 27 ml 0.1 N NaOH and the overall weight brought to 500 g. The specific weight of the dispersion was almost 1, so the error in volume was slight. The mixture was heated to 55° C. with rotation and the system kept at this temperature using a water bath:
a) annealing at 55° C. for 10 min
b) ultrasound (100%) at 55° C. for 20 min The mixture was sterile-filtered while still warm through 0.2μ and stored at from +4° C. to +8° C.
Observations—the dispersion is stable, storage at least 1 year.
It meets all important criteria.
Stability in storage
Filtration under sterile conditions possible
Heat sterilisation possible
Synthesis for auxiliary dispensed with
Auxiliary pharmaceutically known
Auxiliary also has a buffer capacity at pH 5.0

Example Group 4

Fatty Acid Amides of Amino Acids as Negative Charge Carriers

| Oleylphosphocholine | (MG 433.61) |
|---|---|
| Cholesterol | (MG 386.66) |
| N-oleoyl-alanine, Na$^{(+)}$salt | (MG 375.53) |

Example 4 (a)

Ol-PC, 40 mM; Chol 40 mM; N-oleoyl-alanine, 5 mM

| Ol-PC | 40.0 mM; 1.73 g | |
|---|---|---|
| Chol | 40.0 mM; 1.55 g | weighed-in portion: 100 g = 100 ml |
| N-oleoyl-Al | 5.0 mM; 0.19 g | |

Preparation

The weighed-in portion was dissolved in 30 ml $CH_2Cl_2$, the solvent was removed and the residue dried to a constant weight. The residue was brought to a total of 100 g with 0.3 M 1,2-propanediol and heated to 55° C.:
a) annealing at 55° C. for 10 min
b) ultrasound (100%) at 55° C. for 20 min The mixture was filtered under sterile conditions while still warm through 0.2μ and stored at from +4° C. to +8° C.

Example 4 (b)

Ol-PC, 40 mM; Chol 40 mM; N-oleoyl-alanine, 10 mM

| Ol-PC | 40.0 mM; 1.73 g | |
|---|---|---|
| Chol | 40.0 mM; 1.55 g | weighed-in portion: 100 g = 100 ml |
| N-oleoyl-Al | 10.0 mM; 0.38 g | |

Preparation

The weighed-in portion was dissolved in 30 ml $CH_2Cl_2$, the solvent was removed and the residue dried to a constant weight. The residue was brought to a total of 100 g with 0.3 M 1,2-propanediol and heated to 55° C.:
a) annealing at 55° C. for 10 min
b) ultrasound (100%) at 55° C. for 20 min The mixture was filtered under sterile conditions while still warm through 0.2μ and stored at from +4° C. to +8° C.

Example Group 5

Fatty Acid Amides of Glycero-Phospho-Ethanolamine as Negative Charge Carriers

| Oleylphosphocholine | (MG 433.61) |
|---|---|
| Cholesterol | (MG 386.66) |
| N-oleoyl-glycero-phospho-ethanolamide, Na$^{(+)}$salt | (MG 501.57) |

Example 5 (a)

Ol-PC, 40 mM; Chol 40 mM; N-oleoyl-GPE, 5 mM

| | | |
|---|---|---|
| Ol-PC | 40.0 mM; 1.73 g | |
| Chol | 40.0 mM; 1.55 g | weighed-in portion: 100 g = 100 ml |
| N-oleoyl-GPE | 5.0 mM; 0.25 g | |

Preparation

The weighed-in portion was dissolved in 30 ml $CH_2Cl_2$, the solvent was removed and the residue dried to a constant weight. The residue was brought to a total of 100 g with 0.3 M 1,2-propanediol and heated to 55° C.:
a) annealing at 55° C. for 10 min
b) ultrasound (100%) at 55° C. for 20 min The mixture was filtered under sterile conditions while still warm through 0.2μ and stored at from +4° C. to +8° C.

Example 5 (b)

Ol-PC, 40 mM; Chol 40 mM; N-oleoyl-GPE, 10 mM

| | | |
|---|---|---|
| Ol-PC | 40.0 mM; 1.73 g | |
| Chol | 40.0 mM; 1.55 g | weighed-in portion: 100 g = 100 ml |
| N-oleoyl-GPE | 10.0 mM; 0.50 g | |

Preparation

The weighed-in portion was dissolved in 30 ml $CH_2Cl_2$, the solvent was removed and the residue dried to a constant weight. The residue was brought to a total of 100 g with 0.3 M 1,2-propanediol and heated to 55° C.:
a) annealing at 55° C. for 10 min
b) ultrasound (100%) at 55° C. for 20 min The mixture was filtered under sterile conditions while still warm through 0.2μ and stored at from +4° C. to +8° C.

The invention claimed is:

1. A pharmaceutical preparation containing as an active ingredient a) oleylphosphocholine,
   wherein the preparation further contains
   b) cholesterol, and
   c) a negative charge carrier which is oleic acid.

2. The pharmaceutical preparation of claim 1, wherein the preparation is present in the form of liposomes.

3. The pharmaceutical preparation of claim 1, wherein said preparation contains from 10 to 60 mol % of a), 10 to 65 mol % of b) and 3 to 30 mol % of c).

4. The pharmaceutical preparation of claim 1, wherein said preparation further contains a pharmacologically acceptable excipient and/or diluent.

5. The pharmaceutical preparation of claim 1, wherein components a), b) and c) together form 100 mol %.

6. The pharmaceutical preparation of claim 1, wherein said preparation contains the compound a) in an amount of 0.1 to 200 μmol/g.

7. The pharmaceutical preparation of claim 1, wherein said preparation is in a form suitable for intravenous, oral or subcutaneous administration and, in the case of oral administration, is formulated as a tablet or capsule.

8. The pharmaceutical preparation of claim 1, wherein b) is in excess of c).

* * * * *